(12) United States Patent
Goetz et al.

(10) Patent No.: US 8,352,043 B2
(45) Date of Patent: Jan. 8, 2013

(54) METHOD FOR CLOCK MANAGEMENT FOR AN IMPLANTABLE MEDICAL DEVICE

(75) Inventors: Steven M. Goetz, North Oaks, MN (US); Jiaying Shen, Maple Grove, MN (US); Emem D. Akpan, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 510 days.

(21) Appl. No.: 12/501,611

(22) Filed: Jul. 13, 2009

(65) Prior Publication Data

US 2010/0010581 A1    Jan. 14, 2010

Related U.S. Application Data

(60) Provisional application No. 61/080,336, filed on Jul. 14, 2008.

(51) Int. Cl.
*A61N 1/00* (2006.01)
(52) U.S. Cl. ........................................... 607/60
(58) Field of Classification Search ................ 607/60, 607/32, 59
See application file for complete search history.

(56) References Cited

U.S. PATENT DOCUMENTS

| | | | |
|---|---|---|---|
| 4,692,147 | A | 9/1987 | Duggan |
| 5,782,798 | A | 7/1998 | Rise |
| 5,814,014 | A | 9/1998 | Elsberry et al. |
| 2004/0133248 | A1 | 7/2004 | Frei et al. |
| 2005/0103351 | A1 * | 5/2005 | Stomberg et al. ............ 128/898 |
| 2006/0041222 | A1 | 2/2006 | Dewing et al. |
| 2006/0155495 | A1 | 7/2006 | Osorio et al. |

FOREIGN PATENT DOCUMENTS

WO    20060118499 A    11/2006

OTHER PUBLICATIONS

International Search Report and Written Opinion issued Nov. 19, 2009 for co-related PCT Application No. PCT/US09/050370.
U.S. Appl. No. 61/080,427, filed Jul. 14, 2008, "Improved Interface for Implantable Medical Device Programming," Inventor: Touby A. Drew.
Medtronic Brochure, "RestoreUltra", 2008, Brochure Publication No. UC200801088a.

* cited by examiner

*Primary Examiner* — Eric D. Bertram
(74) *Attorney, Agent, or Firm* — Scott A. Marks; Beth L. McMahon

(57) ABSTRACT

An implantable medical device is capable of delivering the therapeutic output to the patient. A controller, programmable by a medical professional, is operatively coupled to the implantable medical device to, in part, program the therapeutic output to be delivered to the patient. The controller has an interface allowing the medical professional to select an amount of the therapeutic output to be delivered to the patient in at least one of the series of discrete timer intervals. However, the therapeutic output deliver to the patient is dependant upon the clock time to which the infusion device is set. In certain situations the infusion device clock time may have inaccuracies that grow over time. The clock time can be reset by the infusion programmer but a method must be in place to determine and account for resetting the infusion device clock time that controls when the therapy will be delivered.

14 Claims, 13 Drawing Sheets

FIG. 7

METHOD FOR CLOCK MANAGEMENT FOR AN IMPLANTABLE MEDICAL DEVICE

RELATED APPLICATION

This application claims the benefit of the filing date of a provisional U.S. Application Ser. No. 61/080,336, filed Jul. 14, 2008.

FIELD

This invention relates generally to an implantable medical device. More particularly, the present invention relates to a computer method and apparatus for updating the clock of an implantable medical device and safety checking the same.

BACKGROUND

Implantable medical devices for producing a therapeutic result in a patient are well known. Examples of such implantable medical devices include implantable drug infusion pumps, implantable neurostimulators, implantable cardioverters, implantable cardiac pacemakers, implantable defibrillators, cochlear implants, and others that now exist or may exist in the future. These devices are intended to provide a patient with a therapeutic output to alleviate or assist with a variety of conditions. Typically such devices are implanted in a patient and provide a therapeutic output under specified conditions on a recurring basis.

One type of implantable medical device is a drug infusion device which can deliver a medication, typically fluid medication, to a patient at a selected site. A drug infusion device may be implanted at a location in the body of a patient and deliver a fluid medication through a catheter to a selected delivery site in the body. Examples of such devices are described in U.S. Pat. No. 5,782,798 to Rise, entitled Techniques for Treating Eating Disorders by Brain Stimulation and Drug Infusion; U.S. Pat. No. 5,814,014 to Elsberry et al., entitled Techniques of Treating Neurodegenerative Disorders by Brain Infusion, each assigned to Medtronic, Inc., Minneapolis, Minn.

Another type of implantable medical device is an electrical stimulation device. An electrical stimulator can also be implanted in the body of a patient and can stimulate selected nerves in the body in accordance with a specified routine. The electrical stimulator may be implanted at a location in the body and deliver electrical stimulation pulses through a lead or leads to a stimulus site. One example of such an implantable electrical stimulation device is Medtronic's RestoreUltra™ neurostimulator.

It is desirable to be able to non-invasively program an implanted medical device, such as a drug infusion device or an electrical stimulation device, in order to change the therapeutic regimen without incurring unnecessary trauma to the patient. An example of such a device is described in U.S. Pat. No. 4,692,147 to Duggan, entitled Drug Administration Device, assigned to Medtronic, Inc., which can be non-invasively programmed to change both the dosage amount and the dosage interval. Verification of the received dosage and interval commands are achieved by means of an audio transducer which is attached to the device case. The implantable drug administration device described in Duggan allows a medical professional to program the delivery rate of a drug contained in the reservoir of the device over a specified interval. The process, however, may be labor intensive.

Non-invasively programmable implantable medical devices are typically programmed using an external programming device, sometimes known as a controller, which can communicate with the implanted medical device through well known techniques such as telemetry. An external controller, or programmer, can be used by a medical professional, for example, to change the therapeutic regimen by increasing or decreasing the amount of fluid medication delivered or by increasing or decreasing the intensity or timing or characteristic of an electrical stimulation signal. Typically, a medical professional interfaces with the external controller or programmer to set various parameters associated with the implantable medical device and then transmits, or downloads, those parameters to the implanted medical device. The external device may also record other information important to the delivery of the therapeutic output although not actually downloaded to the implanted medical device, e.g., patient information, implanted device information such as model, volume, implant location, length of catheter or lead, and other information specific to different devices.

The implementation of a therapeutic program requires timing to be very precise. It has been found that timers may include some amount of time drift. Drifts on the order of +/−15 minutes per year may not be unusual, causing programmed events, such as a bolus from an implantable drug pump, to be off by as much as 15 minutes, in a given year, and up to 105 minutes in pump's typical 7 year life if left uncorrected. In normal drug pump procedures, for example, the pump does not go more than approximately 180 days without being filled. The drift over this time period therefore could be on the order of seven to eight minutes. As may be appreciated, depending on the type of implantable device, the specific programming, and other factors, may make the clock drift more or less significant. However, a system of updating the correct clock time to the drug pump is therefore needed.

BRIEF SUMMARY OF THE INVENTION

One embodiment includes a method for adjusting the clock time of an implantable device, comprising establishing connection between a programmer and the implantable device, comparing a clock time of the programmer to a clock time of the implantable device and evaluating discrepancies between the same, determining whether the discrepancy is greater than a pre-determined threshold, and updating the clock time of the implantable device if the discrepancy is greater than the pre-determined threshold.

Another embodiment includes a method for adjusting the clock time of an implantable device through establishing connection between a programmer and the implantable device, comparing a clock time of the programmer to a clock time of the implantable device and evaluating discrepancies between the same, informing a user if a discrepancy exists, performing an impact analysis analyzing the change in therapy if the clock time of the implantable device was adjusted to the clock time of the programmer, informing the user of the impact analysis and waiting for input from the user based upon the impact analysis, updating the clock time of the implantable device based upon the user's input.

Also included herein is a method for adjusting the clock time of an implantable device including establishing communication between an external device and the implantable device, comparing a clock time of the external device to a clock time of the implantable device and determining whether a discrepancy exists, determining whether the discrepancy is less than a pre-determined threshold, and updating the clock time of the implantable device if the discrepancy is less than the pre-determined threshold.

Another aspect of the invention is a method for updating the clock time of an implantable device that includes establishing connection between an external device and the implantable device, comparing a clock time of the external device to the clock time of the implantable device and determining whether a difference exists, informing a user if a difference exists, determining the impact on a delivery of therapy if the clock time of the implantable device is adjusted to the clock time of the external device, informing the user of the impact, requesting input from the user based upon the impact, and updating the clock time of the implantable device based upon the user's input.

An additional aspect includes a system for delivery therapy comprising an implantable device including device electronics disposed in a housing and means for delivering therapy to a patient, a programmer including programmer electronics disposed in a housing, a communication system including a first portion disposed in the implantable device and a second portion disposed in the programmer, the communication system allowing communication between the implantable device and the programmer, the first portion and the second portion operably connected to the device electronics and the programmer electronics, respectively, and first and second clock electronics disposed in the implantable device and the programmer and operably coupled to the device electronics and the programmer electronics, respectively, the clock electronics each including a computer readable medium containing instructions that when implemented cause the device electronics to check a device clock against the programmer clock and to either automatically adjust the device clock to match the programmer clock or present a clock error signal to a user.

Yet another aspect includes a method for adjusting the clock time of an implantable device, establishing communication between an external device and the implantable device, comparing a clock time of the external device to a clock time of the implantable device and determining whether a discrepancy exists, determining whether the discrepancy is less than a pre-determined threshold, updating the clock time of the implantable device if the discrepancy is less than the pre-determined threshold and calculating and implementing a new simple continuous rate.

BRIEF DESCRIPTION OF THE DRAWINGS

Embodiments of the present invention will hereinafter be described in conjunction with the following drawings wherein like reference numerals denote like elements throughout.

FIG. 7 is an example screen shot presenting issues with the therapy delivered to the patient based upon changing the infusion device clock time is changed.

DETAILED DESCRIPTION OF THE INVENTION

The present invention relates to a method for updating the clock of an implantable medical device 14 using an external programmer 20. In one embodiment, the external programmer 20 may be used by a medical professional to gather information from the medical device 14 and also to program or otherwise download information to the medical device 14. The external programmer 20 may also be known as a controller, programmer, or by other names known to those of skill in the art, or may be any external device that can communicate with the implantable medical device 14 and can assist in updating the clock of the implantable medical device.

The programmer 20 may display information and receive instructions through a user interface that incorporates a standard operating system such as a personal computer. In one embodiment, the external programmer 20 may be used by a medical professional to gather information from the implantable device 14 and also to program or otherwise download information to the implantable device 14. The medical professional may be a doctor, clinician, nurse, or other individual who is responsible for procedures relating to the implantable medical device 14, such as updating the programming, refilling, changing the dosing, or other tasks associated with an implantable device 14. The person using the programmer 20 to extract or input information to the implantable device 14 will be referred to herein as a "user." The programmer 20 may also be known as a controller, a programmer, or by other names known to those of skill in the art.

Figure 1:
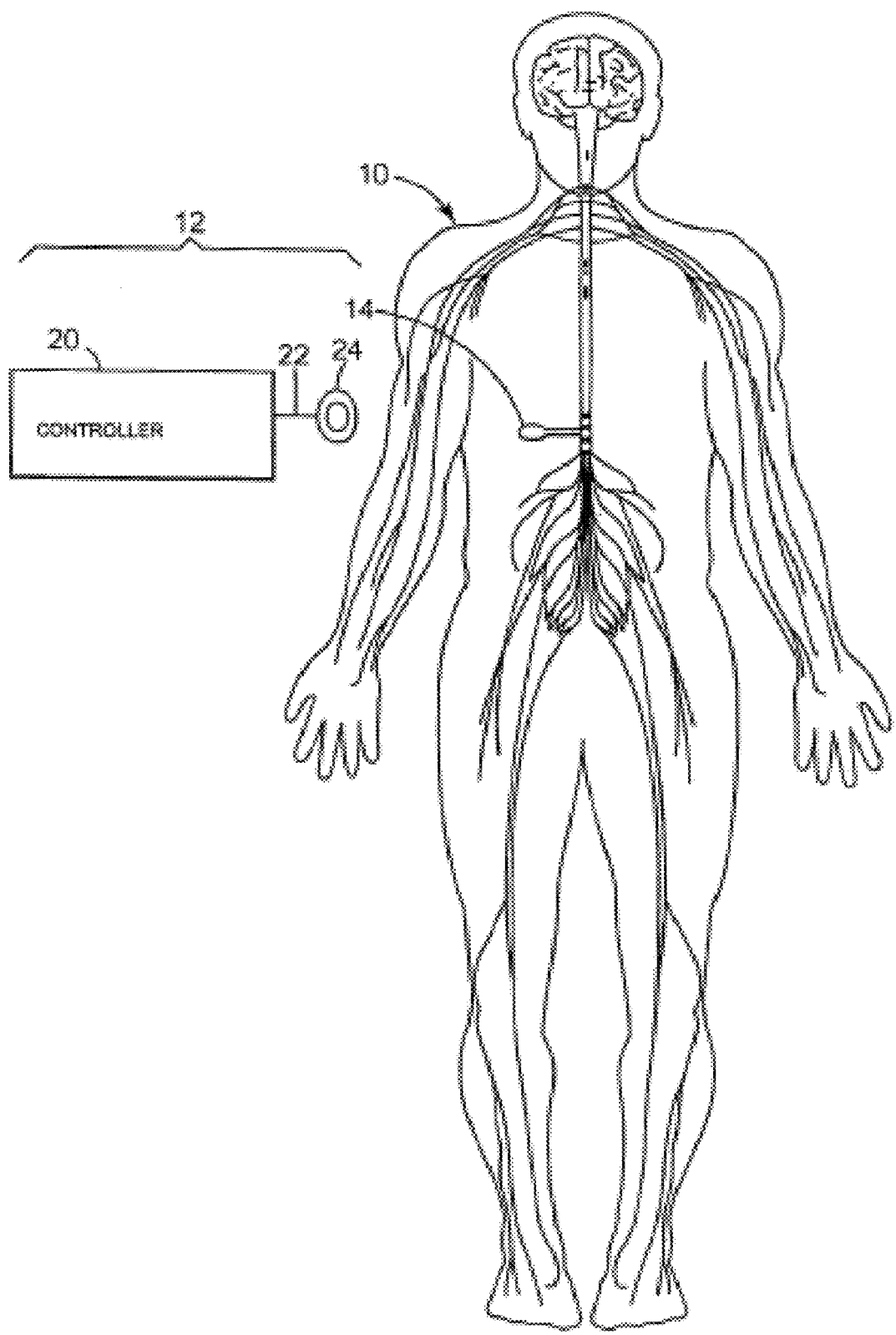
FIG. 1 is a schematic view of an implantable device implanted in a person and a controller.

In one embodiment the programmer 20 may include a remote device 24 placed near to the patient for communication purposes. The remote device 24 may be connected to the programmer 20 through a connector 22, such as a cord or a standard USB cable, or through a wireless communication protocol. The remote device 24 may in turn communicate with the implantable device 14. The implantable device 14, programmer 20, remote device 24, and connector 22 may be collectively referred to as system 12. FIG. 1 is therefore a schematic view of a drug infusion system 12 with implantable drug infusion device 14 implanted within the body of patient 10. Methods of communicating with implanted treatment devices using radio frequency telemetry, inductive communication, and other formats in order to program such implanted drug infusion devices are well known in the art. The programmer 20 may be a dedicated handheld device or workstation or, in other embodiments, the programmer 20 may be a standard personal computer or other device that can operate an interface as described herein. The screens and operating system that are run on the programmer 20 may the same or similar for both.

With regard to references in this specification to computers, the computer, if included, may be any standard computer including standard attachments and components thereof (e.g., CD drives, etc.). The computer may include a mouse and keyboard and may include touch screen or other interfaces as known to those in the art. When various options on the following described pages are selected by the user, the user may use any compatible input device. The following description will reference the programmer 20 connected to remote device 24 though it should be understood that the programmer 20 may include a computer workstation and a remote device 24 connected thereto. However, this description will generally describe the programmer 20 as a stand alone hand held device.

In the present description the system 12 may be capable of delivering a therapeutic output to a patient 10 through the implantable medical device 14. The programmer 20 is operable to specify the therapeutic output to be delivered. The programmer 20 allows the medical professional to interface with the implanted medical device 14. Implantable device 14 can be any of a number of medical devices such as an implantable therapeutic substance delivery device, implantable drug pump, implantable electrical stimulator, cardiac pacemaker, cardioverter or defibrillator, for example. In other embodiments, the implantable medical device 14 may instead be a sensor, recorder, analyzer, monitor or other medical device that does not provide therapy. For purposes of illustration, the present invention will be described with respect to an implantable drug infusion device. However, it should be recognized and understood that the present invention has applicability to other types of implantable medical devices, e.g., implantable electrical stimulators.

FIG. 1 is therefore a schematic view of a drug infusion system 12 with implantable drug infusion device 14 implanted within the body of patient 10. Drug infusion device 14 may be programmable through a telemetry link from programmer 20, which may be coupled via a conductor 22 to a radio frequency antenna 24. Drug infusion device 14 could be, but is not limited to being, a pump for infusing fluid medication into a patient's body.

Figure 2:
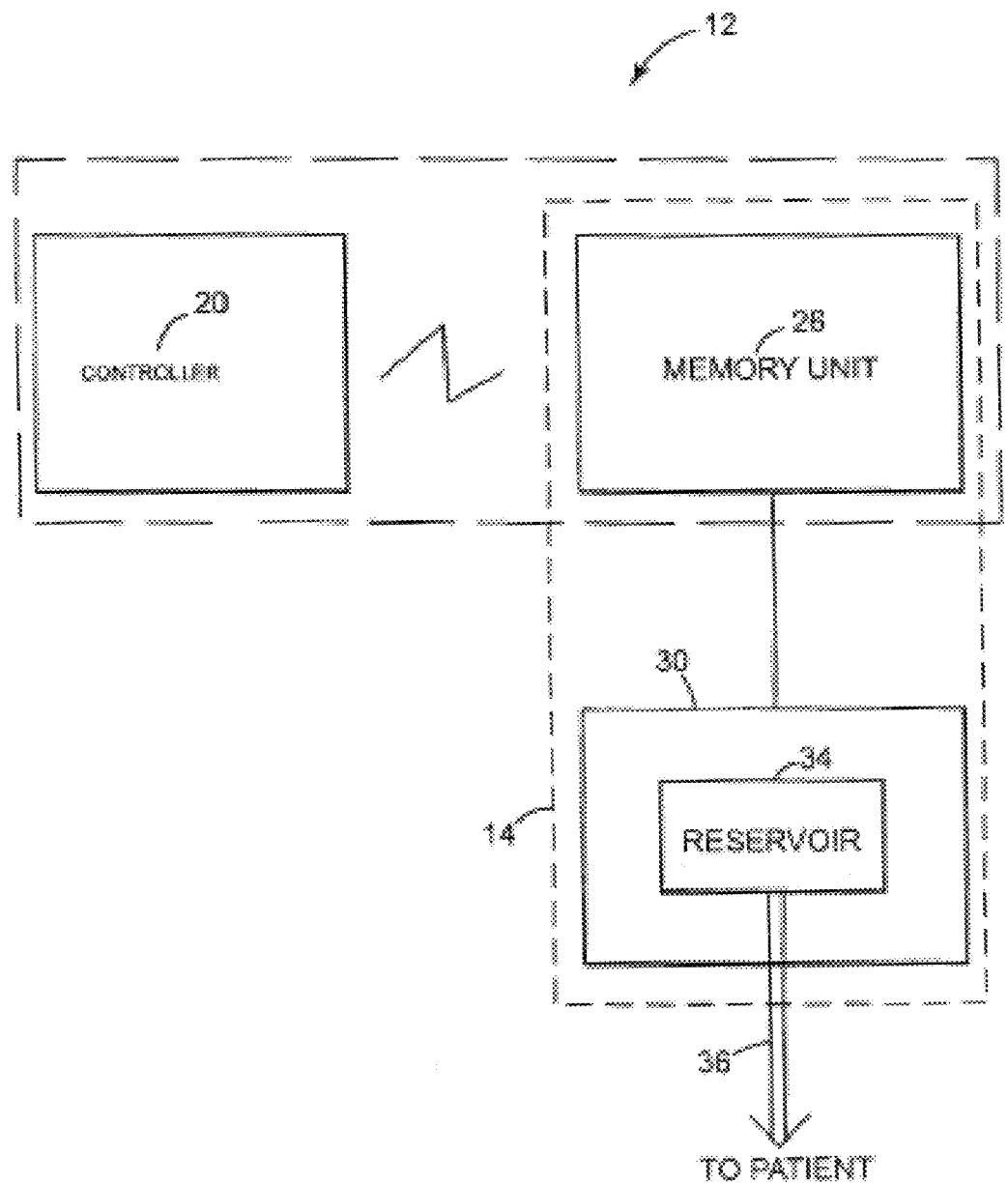
FIG. 2 is a block diagram of the system of FIG. 1.

FIG. 2 is a block diagram of drug infusion system 12 having an implantable drug infusion device 14. Drug infusion device 14 may include an internal memory unit 26 containing memory and programming that may provide instructions to drug delivery module 30. External programmer 20 may act as an input-output device for drug infusion device 14 and also provide computational support for memory unit 26. In general, drug delivery module 30 is a pump for infusing a fluid medication, including a drug or a combination of drugs, to patient 10. Drug delivery module 30 has a reservoir 34 for holding the fluid medication to be infused and is coupled to patient 10 through catheter tubing 36. Such drug delivery modules 30 are well known in the art. As may be appreciated, the drug infusion device 14 may include other components, such as a battery, remote charging equipment, etc., that are not shown here.

Memory unit 26 and programmer 20 may operate together to control drug delivery module 30 in the delivery of fluid medication to patient 10. In general, drug delivery module 30 is a pump for infusing a fluid medication, including a drug or a combination of drugs, to patient 10. Drug delivery module 30 has a reservoir 34 for holding the fluid medication to be infused and is coupled to patient 10 through catheter tubing 36. Such drug delivery modules 30 are well known in the art.

Memory 26 may receive programming information from programmer 20 through conventional means such as radio frequency telemetry. Programming information, once stored in memory unit 26, provides the dosing regimen to be performed by drug delivery module 30. Similarly, techniques for non-invasively communicating between controllers 20 and implanted drug infusion devices are also well known.

Programmer 20 may require certain inputs of data or information from a medical professional in order to adequately and fully control an implanted medical device. The types of information input can range from patient information, e.g., to keep track of programming regimens among various patients, implantable medical device type and model, and perhaps serial number, capacity or reservoir size, catheter volume, implantation date and implantation location and/or orientation, as well as information related to the programmability functions of the implanted medical device. If the implanted medical device is a drug infusion device, information may need to be input or obtained regarding fluid medication prescription, kinds and amounts or concentrations of fluid medications, amount of fluid medication filled into the reservoir, the infusion program including constant or variable dosage, daily changes, and patient administered options such as boluses. Further, information may also need to be obtained regarding a special initial infusion, commonly referred to as a prime bolus, to account for the initial volume of fluid contained in the catheter which may or may not be the same as the fluid medication contained in the reservoir. Still further, upon refilling the implanted drug infusion device with a new supply of fluid medication, information may be needed regarding a special interim infusion, commonly referred to as a bridge bolus, to account for any change in kind or concentration of fluid medication. Alarms may need to be programmed or set or silenced regarding various anomalies that may occur during programming or infusion. And still further, information may need to be supplied or displayed regarding refill procedures, such as the estimated time to refill or estimated time to battery replacement or explanation. These types of items are generally referred to as tasks throughout this description. As can be seen, there may be a number of variables involving a not insignificant amount of information.

Various procedures may need to be undertaken by a medical professional using the programmer 20. As an example, the medical professional may know that the drug infusion device has been newly implanted into the patient and needs to be set up and initially programmed. As another example, the medical professional may know that the drug infusion device has just been refilled with a different fluid medication, kind or concentration, and needs to be re-programmed. It can be recognized that each of these medical procedures may require a different set of tasks to be performed in order to accomplish the particular procedure involved. For example, an initial implantation procedure may require data to be input regarding the patient's name and particulars. However, during a refill procedure, information regarding the patient may not need to be reviewed or modified unless a change has occurred, as by a name change associated with marriage, for example. As another example, an initial implantation procedure typically will require the use of a prime bolus but not a bridge bolus. Conversely, a refill procedure may require the use of a bridge bolus but not a prime bolus.

In an embodiment infusion device 14 there may be two blocks of memory contained in the infusion device 14 that contain date and time information. One memory block may be the programmer time date memory and the other memory block may be the pump time memory. The pump time memory may include information such as the amount of time since the battery was connected, the time of day, and a cyclic reduction check mechanism to check the time information. The programmer time date memory may include similar information, such as number of minutes from battery connection, programmer time and date, time zone, and a similar check system. In one operating mode the therapeutic delivery is controlled by the pump time memory and the time of day contained in that memory block. The programmer time of day memory block may keep a concurrent memory system that is updated when the infusion device 14 is connected to the programmer. In one embodiment the pump memory block may be updated each time the infusion device 14 communicates with the programmer 20. The updated programmer time date memory of the infusion device 14 may or may not be automatically pushed to the pump time memory block. For purposes of the present disclosure the operation of the dual memory blocks of the infusion device 14 will not be discussed in detail. For purposes of simplicity the present description will only discuss the of updating the overall infusion device 14 clock in terms of one system wide update. However, as may be appreciated, various other steps may be required internal to the infusion device 14 to push the updated time from the programmer time memory block to the pump time memory block depending on the structure of the specific system. When this disclosure states that the infusion device 14 clock time is changed it therefore will be read to mean that the clock time of the infusion device 14 that controls the delivery of therapy is being updated.

Various types of programmers 20 may include a number of different displays that include a number of different welcome screens, task selection guides, ways to interrogate the infusion device 14, etc. Such programmers may be described in U.S. Ser. No. 11/206,654, filed on Aug. 18, 2005, or U.S. Patent Application No. 61/080,427, titled "Improved Interface for Implantable Medical Device Programming," filed Jul. 14, 2008, the entirety of which are both hereby incorporated by reference. The present description will focus on those screen shots and steps that are required for updating the clock time of the infusion device 14.

Figure 4:
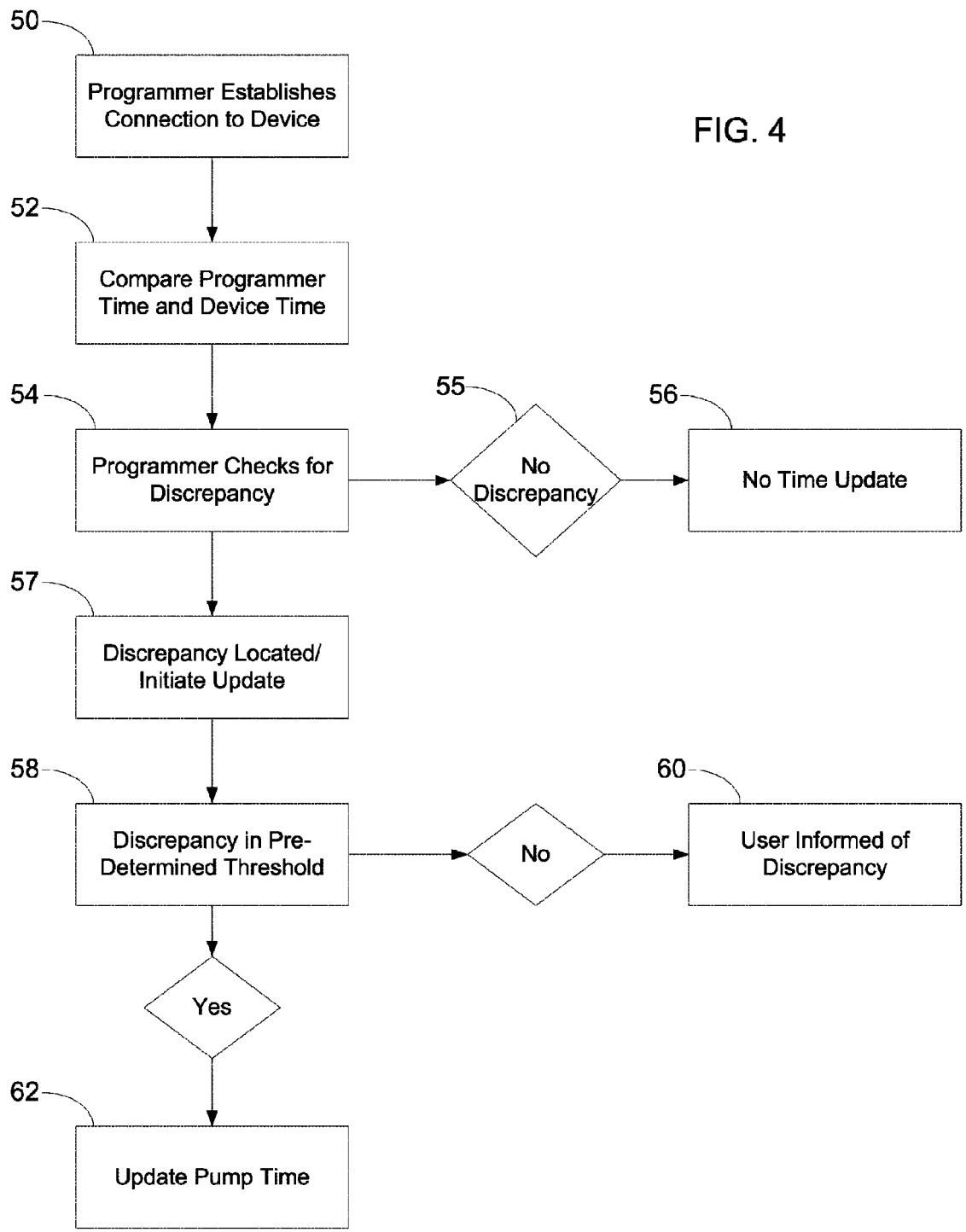
FIG. 4 is a flow diagram of one embodiment of the present invention.

As illustrated in FIG. 4, one embodiment may be directed towards those situations where the infusion device 14 clock time discrepancy may be changed depending on whether it is greater than or less than a certain threshold. The programmer 20 may first establish connection to the device (block 50) in a standard manner. As part of establishing the communication between the programmer 20 and the infusion device 14, the programmer may query the infusion device 14 for the infusion device 14 clock time (block 52) and then check the infusion device 14 clock time against the programmer 20 clock time for any discrepancies (block 54). If no discrepancy is located (block 55) then no time update would be initiated (block 56). However, if a discrepancy is located (block 57) then a clock time update may be initiated.

In one embodiment, if the time clock discrepancy between the infusion device 14 and the programmer 20 is less than a certain threshold (block 58), the infusion device 14 time clock may be updated automatically (block 62). It may be determined that a time discrepancy of only seconds or minutes will not have a serious enough effect on therapeutic output to the patient to warrant further consideration before an update is entered. Depending on the type of implantable medical device (drug pumps, stimulators, etc.), patient or clinician preferences, therapeutic input administered (what kind of stimulation, what kind of drug), for what purpose (pain management, movement disorders, etc.), the time discrepancy threshold for automatically updating the clock time may be different. In addition, the therapeutic program may affect such a change as well. If, for example, the time is incorrect for a drug infusion device that is programmed for a simple continuous drug delivery, no time change will ever affect the therapy the patient is receiving, and can therefore be changed automatically.

Figure 11:
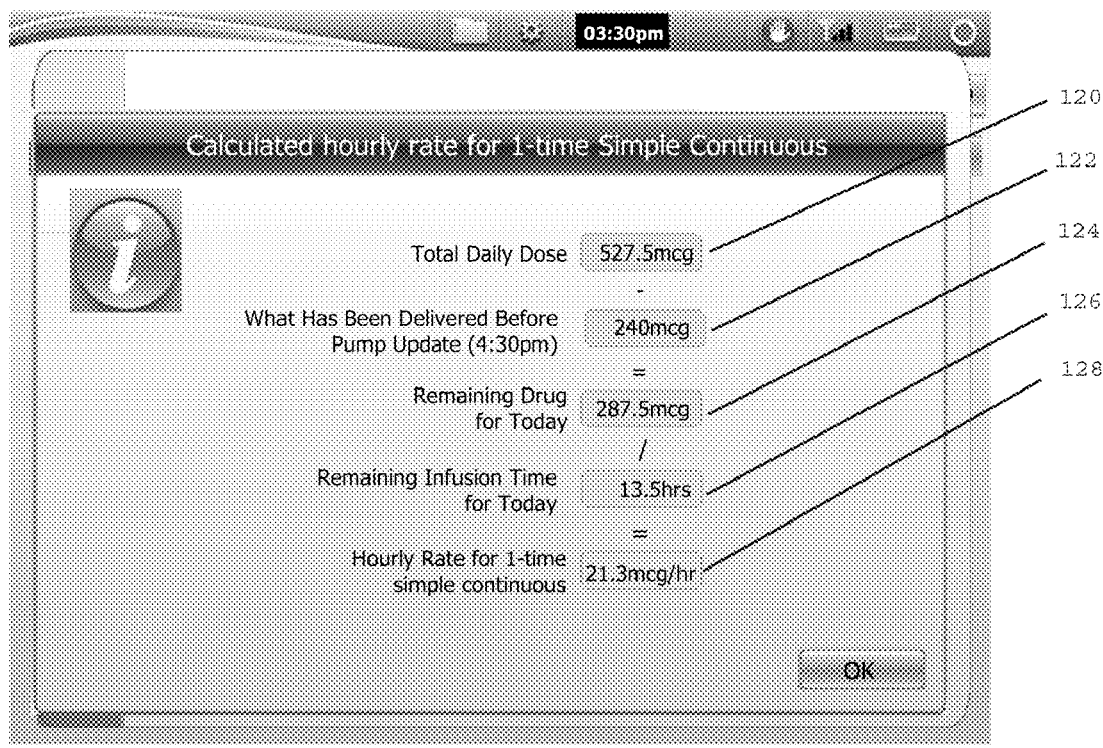
FIG. 11 is a screen shot illustrating how a new simple continuous rate can be calculated.
Figure 12:
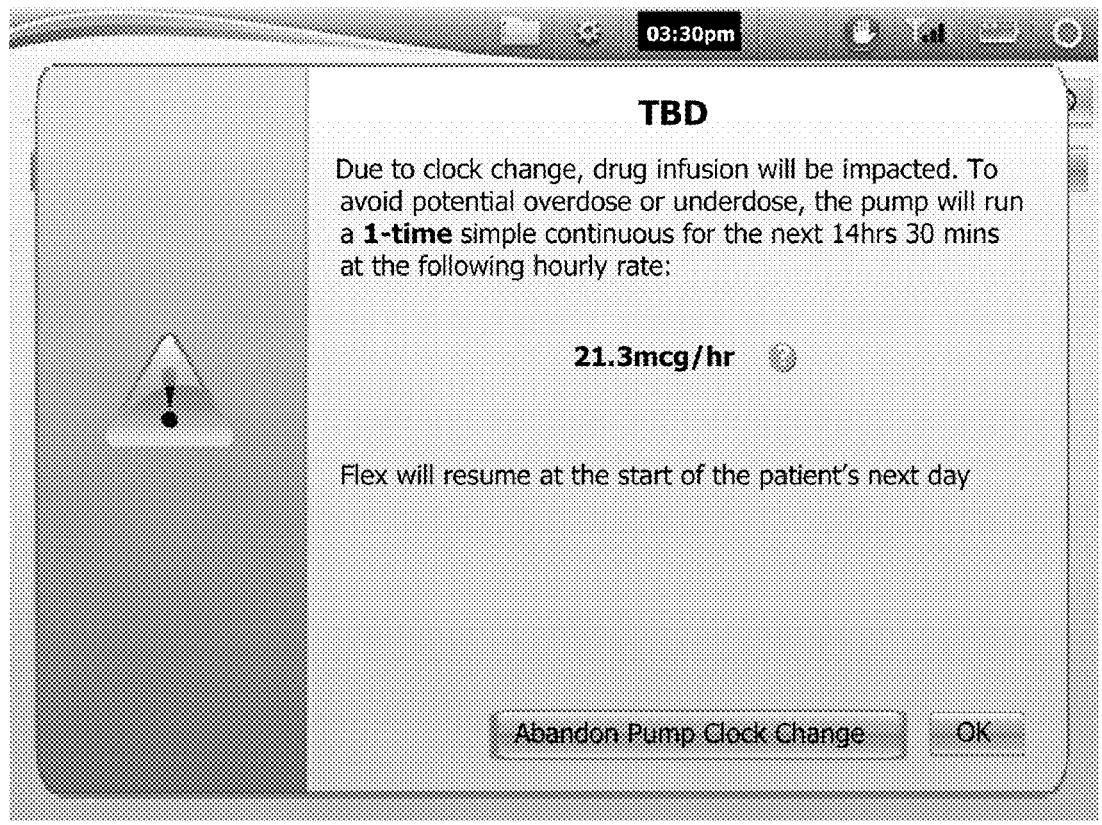
FIG. 12 is a screen shot showing the new calculated continuous rate from FIG. 11.
Figure 13:
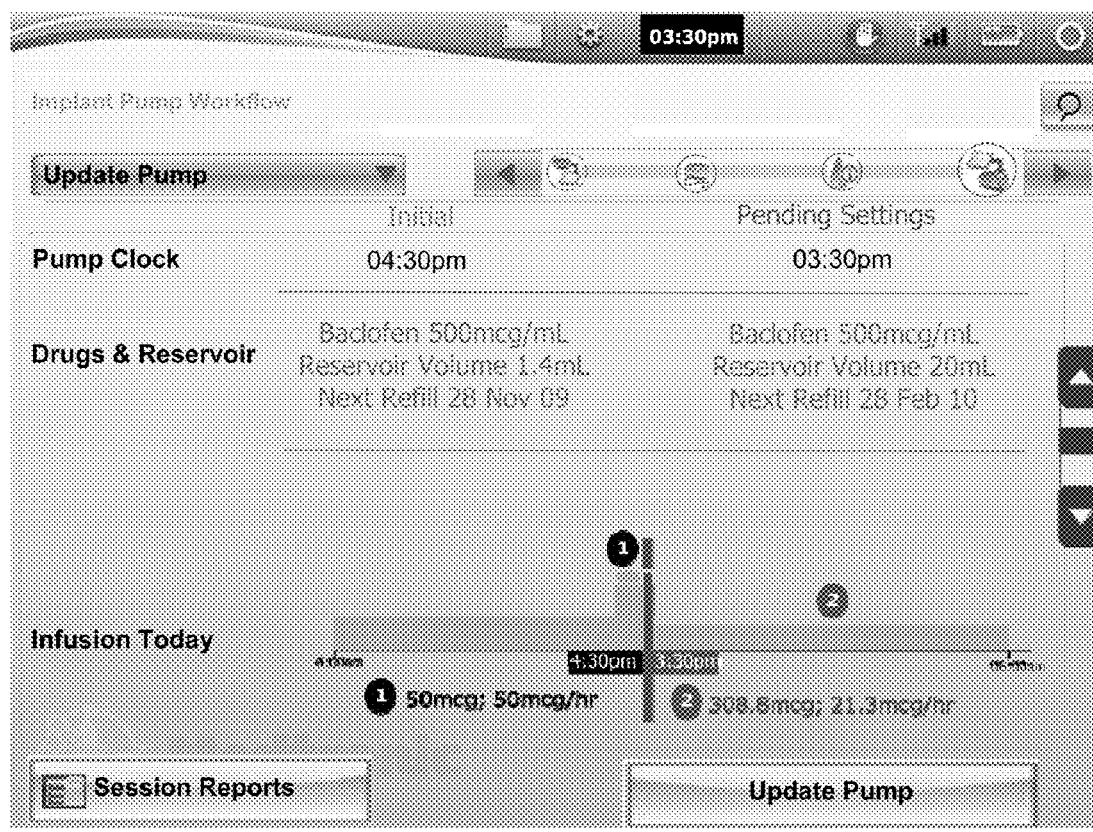
FIG. 13 is a screen shot showing the effect of instituting the newly calculated rate from FIG. 1.

In a further embodiment the programmer 20 or the infusion device 14 may calculate a suggested new rate to overcome or even out any therapeutic changes that may result from a change in the clock time. As illustrated in FIG. 11, the total daily dose 120 for the current day can have the amount of material delivered to that point in the day 122 subtracted out to achieve a remaining programmed drug dose 124 for the day. Likewise, the remainder of the infusion for the day can be added to arrive at the same number. Dividing the remaining drug 124 amount that is to be delivered by the total infusion time left for the day 126 results in a simple continuous hourly rate 128 for the remainder of the day that provides the previously programmed amount of drug. (In the embodiment shown in the figures the program runs on a 24 hour schedule starting a 6 a.m.) Providing the user with an option to deliver the same amount of drug over time for the remainder of the day, but at a simple continuous rate rather than at a rate that may include variations, may allow for the clock time to be updated without exposing the patient to any under or over doses during that period. In the present embodiment the normal drug delivery program can start again at the beginning of the normal program day (6 a.m.), reverting back to the day/night, flex or other pattern that is normally utilized. The change in the rate to the new simple continuous calculated rate may be shown in FIG. 12 or graphically as illustrated in FIG. 13.

In still further embodiments, the user may request that the pump clock of the infusion device 14 be corrected on an incremental basis. Rather than setting the clock to immediately jump to the new (correct) time, either at the time the user programs the clock change or at a later time when the patient may be sleeping or utilizing a pump rate more amenable to a clock change, the pump clock can make up the time differential incrementally. The pump clock may be set to gain or lose some set amount of time per designated period, such as gaining or losing one minute per hour until the pump clock time is corrected. As may be appreciated, such a gain or loss may be spread out over the entire preselected period, or may be done at the very beginning of each set of periods. For example, a gain or loss of one minute per hour may be done over the entire hour or may be done at a designated point during each hour, whereby the pump clock jumps forwards or backwards one minute at the designated spot during the hour.

In those cases where the time clock for the infusion device 14 is automatically updated, the programmer 20 may inform the user that the time has been updated automatically. The user may be informed of how much the infusion device 14 clock time was adjusted. In some embodiments the user may be required to acknowledge the fact that the time was updated. In further embodiments the user may not be notified of an automatic clock time adjustment.

Figure 3:
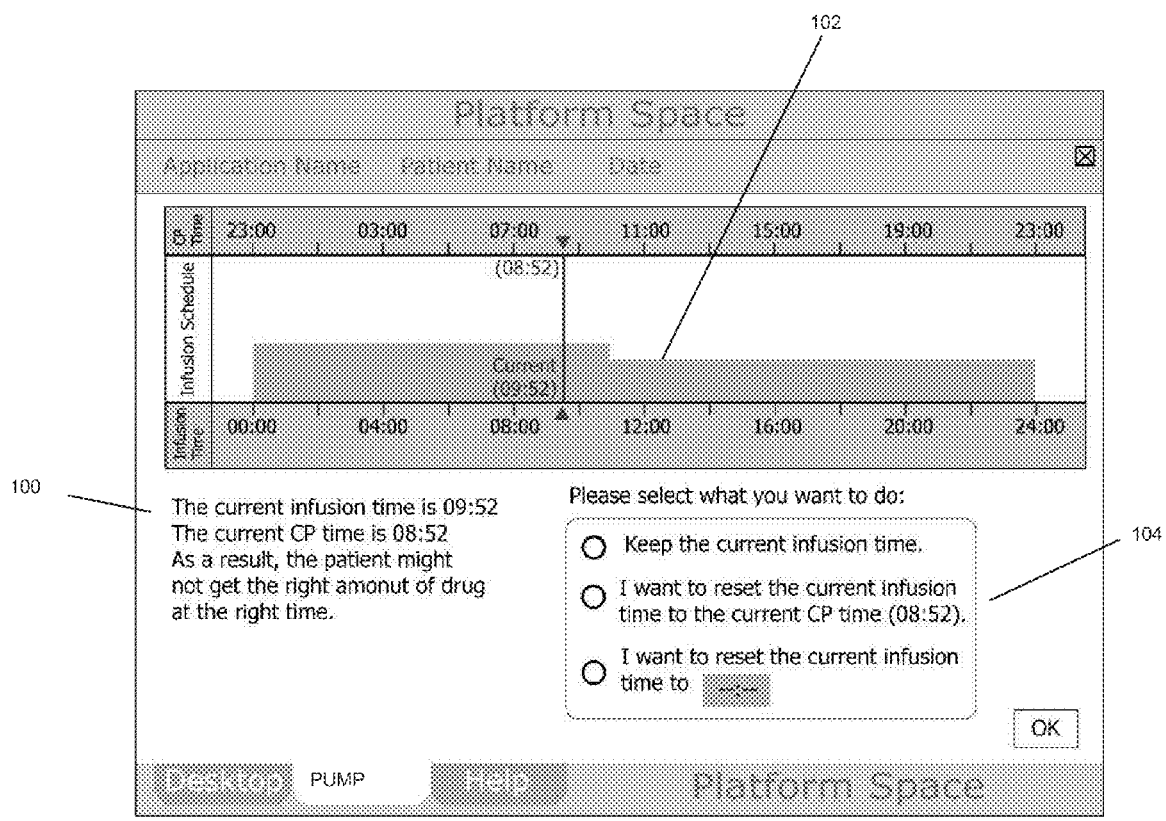
FIG. 3 is a screen shot of one example illustration depicting the time discrepancy information located by a programmer.

In further embodiments, wherein the clock time discrepancy is outside of a certain threshold, or if no threshold has been set, the user may be informed of the discrepancy (60) utilizing a screen shot similar to that shown in FIG. 3. The illustrated screen shot may be presented by the programmer 20 when a discrepancy exists between the clock time for the programmer and the clock time for the infusion device 14. As illustrated, the information provided to the user may include the time discrepancy in both numerical terms 100 (9:52 versus 8:52) and also in graphical terms 102. Other information may be stored in the pump and retrieved and displayed in order to aid in the decision making process. Such information might include the time zone in which the pump time was last set and whether daylight savings was in effect when the pump time was previously adjusted. Providing a display of such information, along with a display of the equivalent information for the current programmer clock may aid the user in making the most appropriate decision for two common causes of pump/programmer time discrepancy. As may be appreciated, the numerical information and the graphical information may be utilized and mixed in a variety of ways in a number of different screen shot formats. The infusion time is defined as the clock time for the infusion device 14. The "CP" time is the clinician programmer, or programmer 20, clock time.

The graphical display may help the user to recognize those infusion program events that may be impacted by changing the clock time for the infusion device 14. The screen shot as illustrated may further present the user with options to address the infusion device 14 clock time discrepancy. In the present example screen shot the user is presented with the options of keeping the infusion device 14 clock time, resetting the infusion device 14 clock time to the programmer 20 time, or resetting the infusion device 14 clock time to a third time. With respect to resetting the clock time of the infusion device 14 to a third time, the user may have determined that neither the programmer 20 time nor the infusion device 14 time were accurate.

Figure 5:
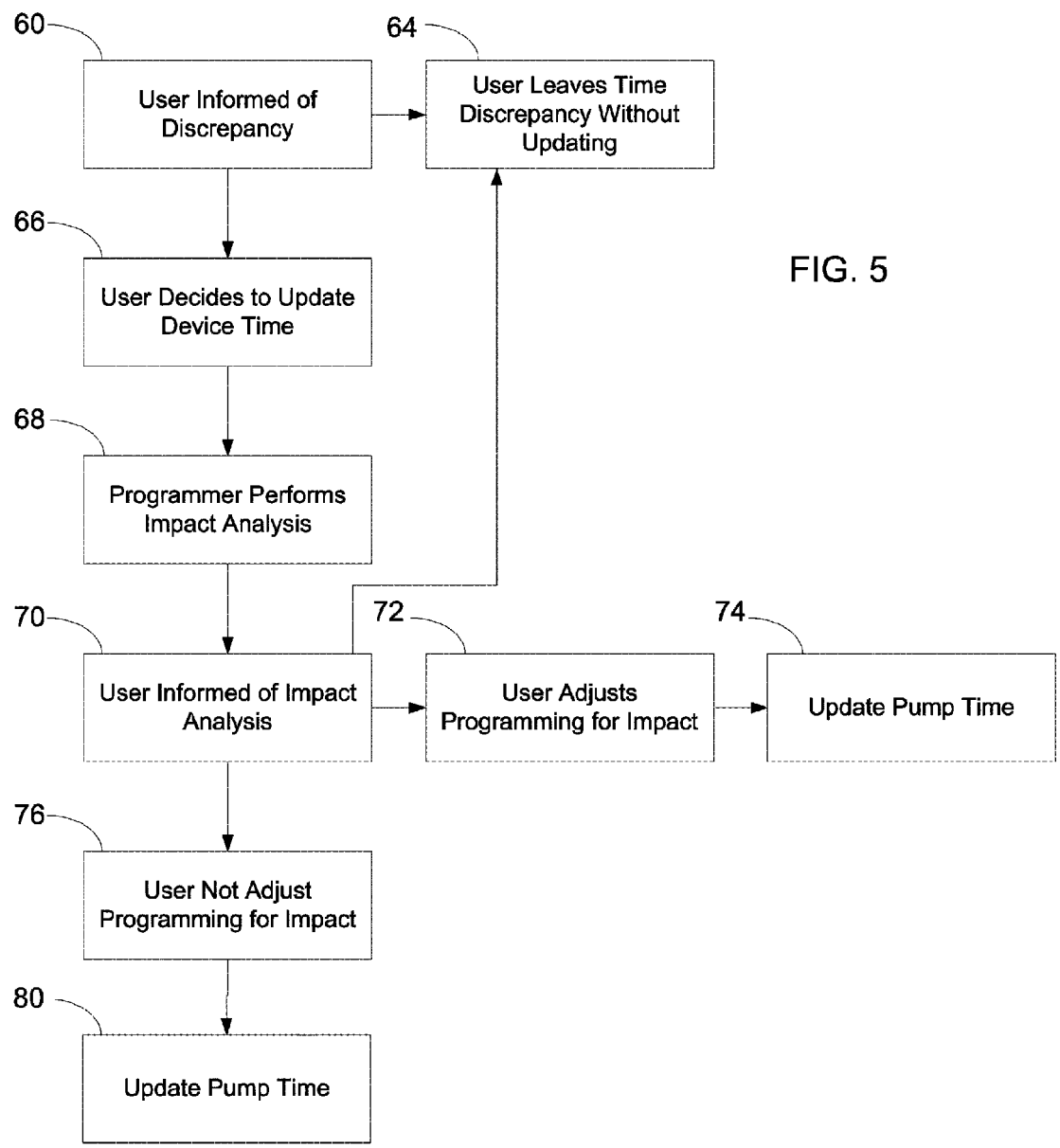
FIG. 5 is a flow diagram of another embodiment of the present invention.

FIG. 5 illustrates a flow diagram representing the steps that may be undertaken when a user is informed of the infusion device 14 clock time discrepancy (block 60) that has not been automatically updated. At this point the user may determine to leave the time discrepancy and keep the current infusion time (block 64). There may be several reasons why the user does not want to update the clock time for the infusion device 14. For example, the user may not be the patient's primary clinician, the user may believe that the time discrepancy is not enough to warrant a change at that time, the patient may be in a different time zone than where the patient normally lives, or for other reasons. Alternatively, the user may determine to update the clock time for the infusion device 14 (block 66).

Figure 6:
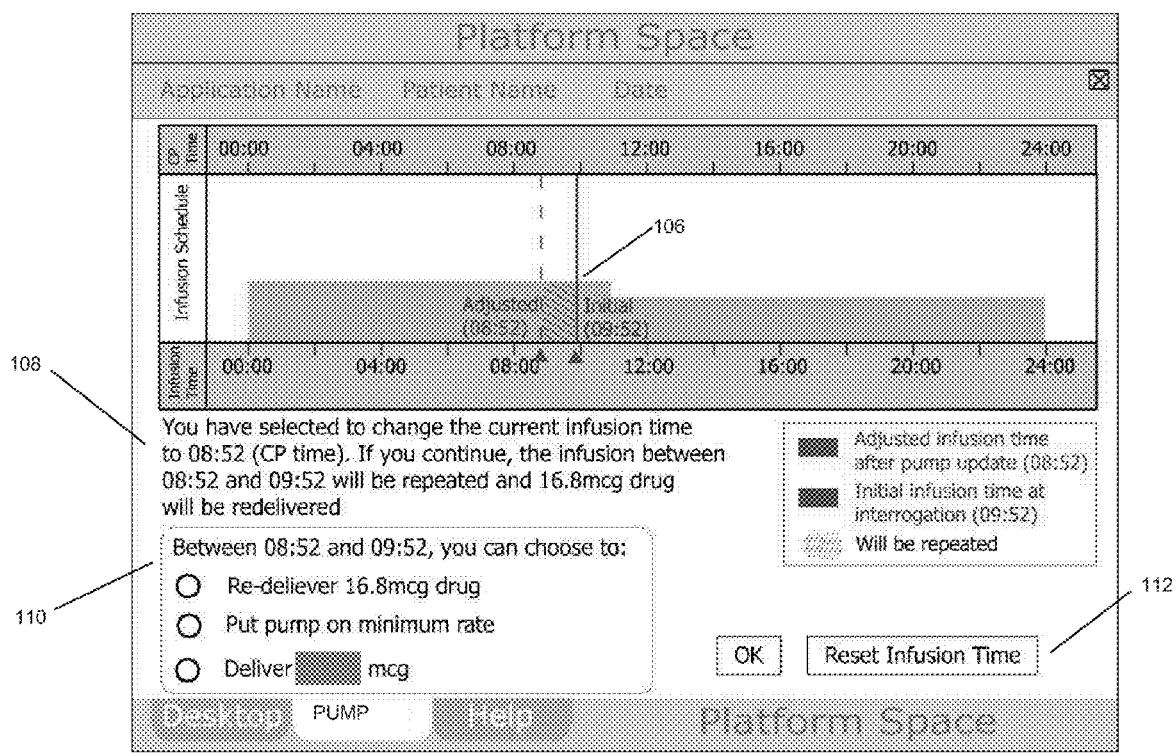
FIG. 6 is a screen shot of one example showing the effect of the clock time change and some options for changing the infusion program.

If the user decides to update the clock time for the infusion device 14, the programmer 20 may do an impact analysis (block 68) to determine the effect that the new clock time will have on the therapeutic output delivered to the patient. As illustrated in the screen shot in FIG. 6, the impact analysis information may be presented in a combination of visual or graphical representations 106 and written description 108 (block 70). In the illustrated example, the time change of one hour will cause a repeat of infusion programming therapy that has already been delivered, and delay a reduction in the therapy being delivered. As may be appreciated, the graphical representation may be highlighted using a variety of colors, shading, and other features.

Once informed of the time change impact (block 70), the user may be given a number of choices as to how to adjust an infusion time 110, including repeating the previously programmed rate or adjusting the infusion program (block 72) by either placing the pump on a minimum rate, stopping the pump for a period of time, or setting a new dosage rate. The user may select one of these options by clicking on the appropriate selection (FIG. 6) and then checking an icon 112. As may be appreciated, more complicated ways of adjusting the infusion program (block 72) may be undertaken besides going to a minimum dosage rate or delivering a constant new dosage. In some embodiments the user may decide to set an increasing or decreasing titration-type rate, a periodic rate, or a bolus rate.

Figure 7:
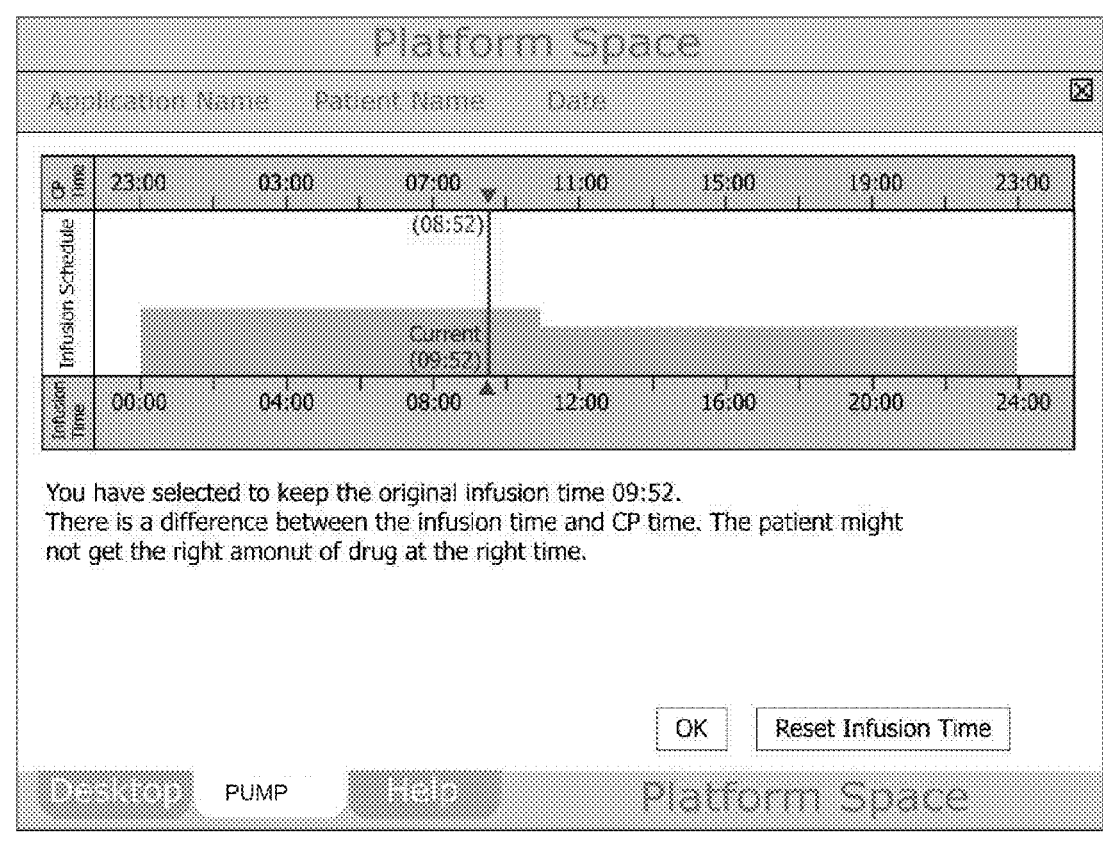

In further embodiments the user may also decide to not change the clock time for the infusion device 14 after the user is presented with the impact analysis, or the options for how to implement the clock change, instead deciding to leave the time discrepancy in place (block 64). A screen such as is shown in FIG. 7 may be presented to the user to inform the user of the effect on the therapy delivered to the patient if the user declines to change the infusion device 14 clock time. After the user has update the infusion program (block 72) the clock time for the infusion device 14 may be updated (block 74).

If the user determines to not adjust the programming at this time (block 76), the user may still update the clock time of the infusion device 14 while leaving the current infusion program in place. The programmer 20 may at this point display a verification screen (not shown) to the user to highlight that the user is going to proceed without adjusting the infusion program to account for the change in clock time.

In still further embodiments, the user may have the option of resetting the infusion device 14 clock time during a later point in the day. Rather than having the patient 10 return to the office where the user is working, the programmer 20 may be able to require the infusion device 14 pump clock to reset to a new time at a point after the patient 10 has left the office. A later time could be selected so as have minimal or no impact on the delivery of therapy, such as when there is no bolus or other change in infusion that will be effected, such as during a period of a constant or simple continuous infusion rate, or to be instituted when the patient is sleeping and therefore causing minimal disturbance.

In another embodiment, time discrepancies could be detected outside of the clinic when a patient uses a patient therapy manager or other instrument allowing patient controlled analgesia. In such an embodiment, whether the infusion device 14 clock time is adjusted might be limited to certain types of discrepancies (i.e., 1 hour shifts for daylight savings, integer changes in hour for time zone purposes). Further, as it is inappropriate for a patient to evaluate and implement advanced means of accommodating an impact in infusion due to time change, the patient therapy manager might block adjustments in the pump clock at times where such an adjustment would have an impact (i.e. only allow changes at times well away from changes in infusion pattern). A given patient's ability to adjust his or her therapy in this way might be further limited to certain drugs, therapies, infusion patterns, or by clinician preference.

Figure 8:
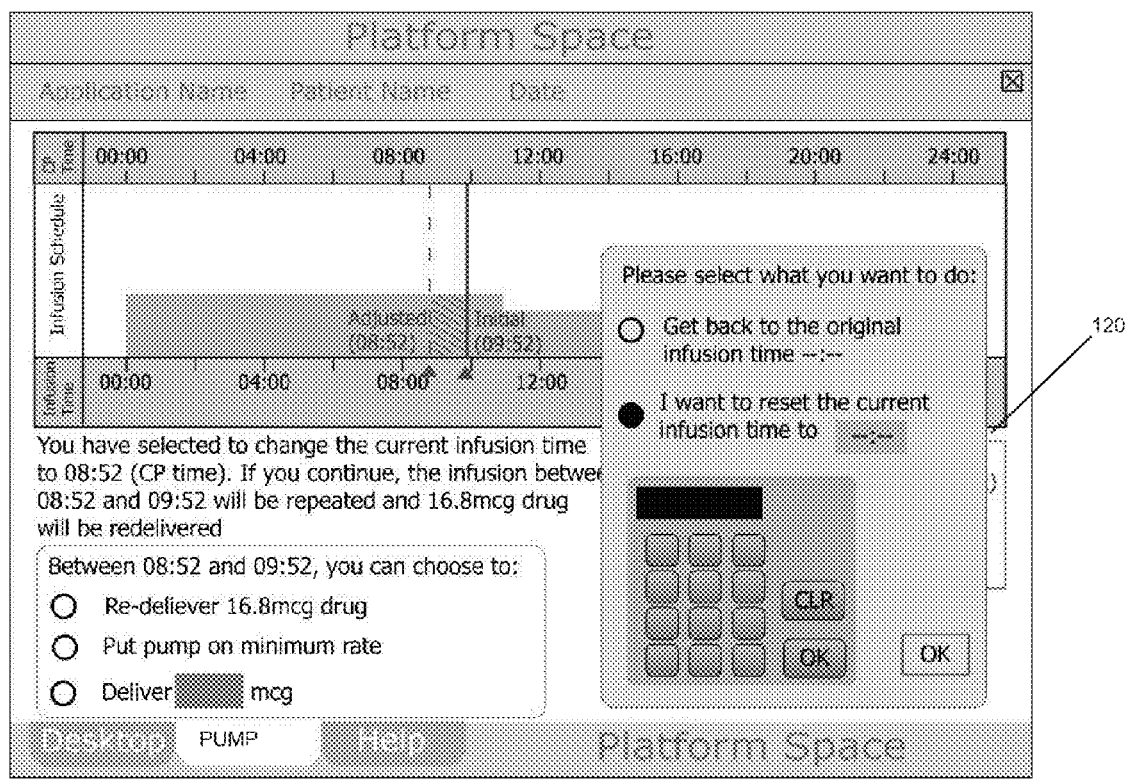
FIG. 8 is an example screen shot illustrating one manner for inputting a new time to change the infusion device clock time.

As previously discussed, the user may wish to set a new time for the infusion device 14 clock time. FIG. 8 may illustrate an example screen for inputting a new time. As illustrated, a pop-up window 120 may include selectable icons for inputting the new time.

Figure 9:
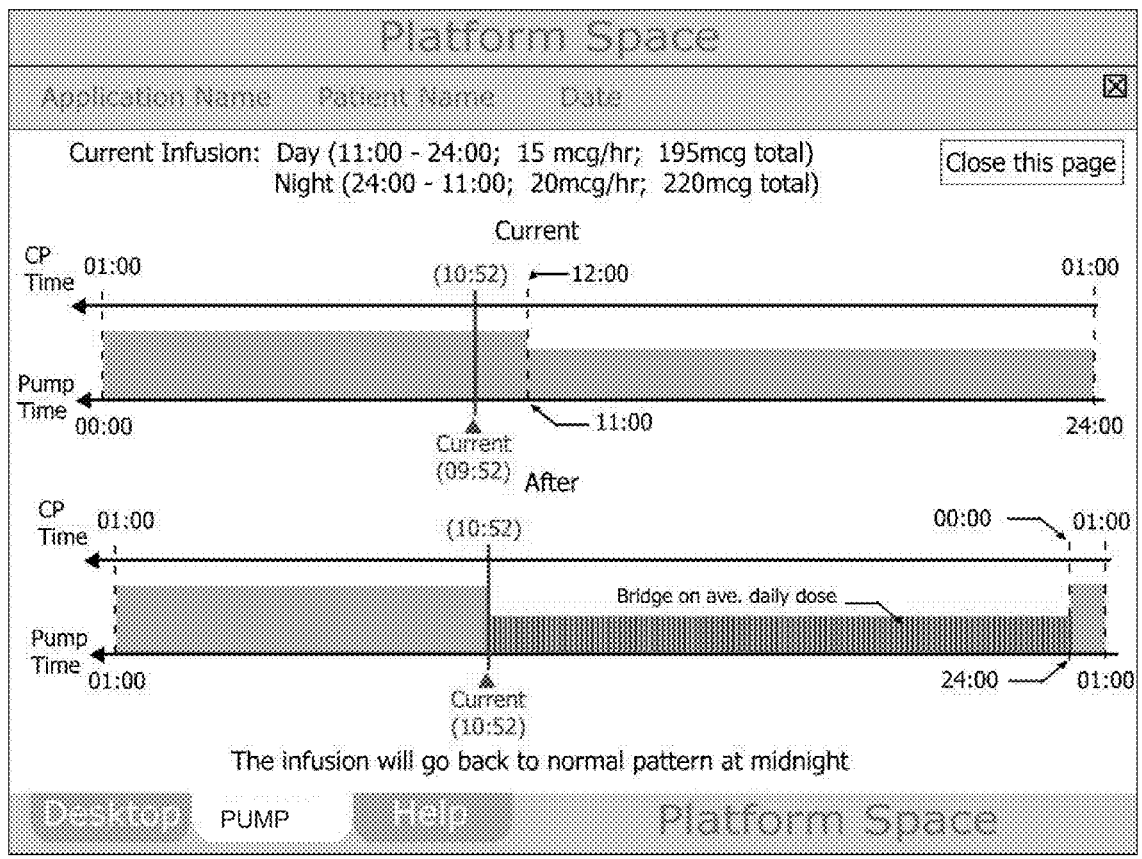
FIG. 9 is an example screen shot that may be utilized to compare the current infusion program to a new infusion program based upon an updated clock time.

If the user desired to enter in a new infusion program to support the time change, a similar pop-up window as shown in FIG. 8 may be utilized. Such a new infusion program may be known as a bridge as it provides a transition between the old clock time and the new clock time. If a bridge infusion rate were entered a screen such as shown in FIG. 9 may be utilized to compare the current infusion program to the new infusion program that will take effect once the new time and dosage information is entered into the infusion device 14. As may be appreciated, such a screen may also allow for the user to cancel the new bridge infusion program if it does not meet the needs of the user or patient. In still further embodiments, the bridge infusion may be selected using a graphical user input to modify the dosage amount or the duration of the bridge.

Figure 10:
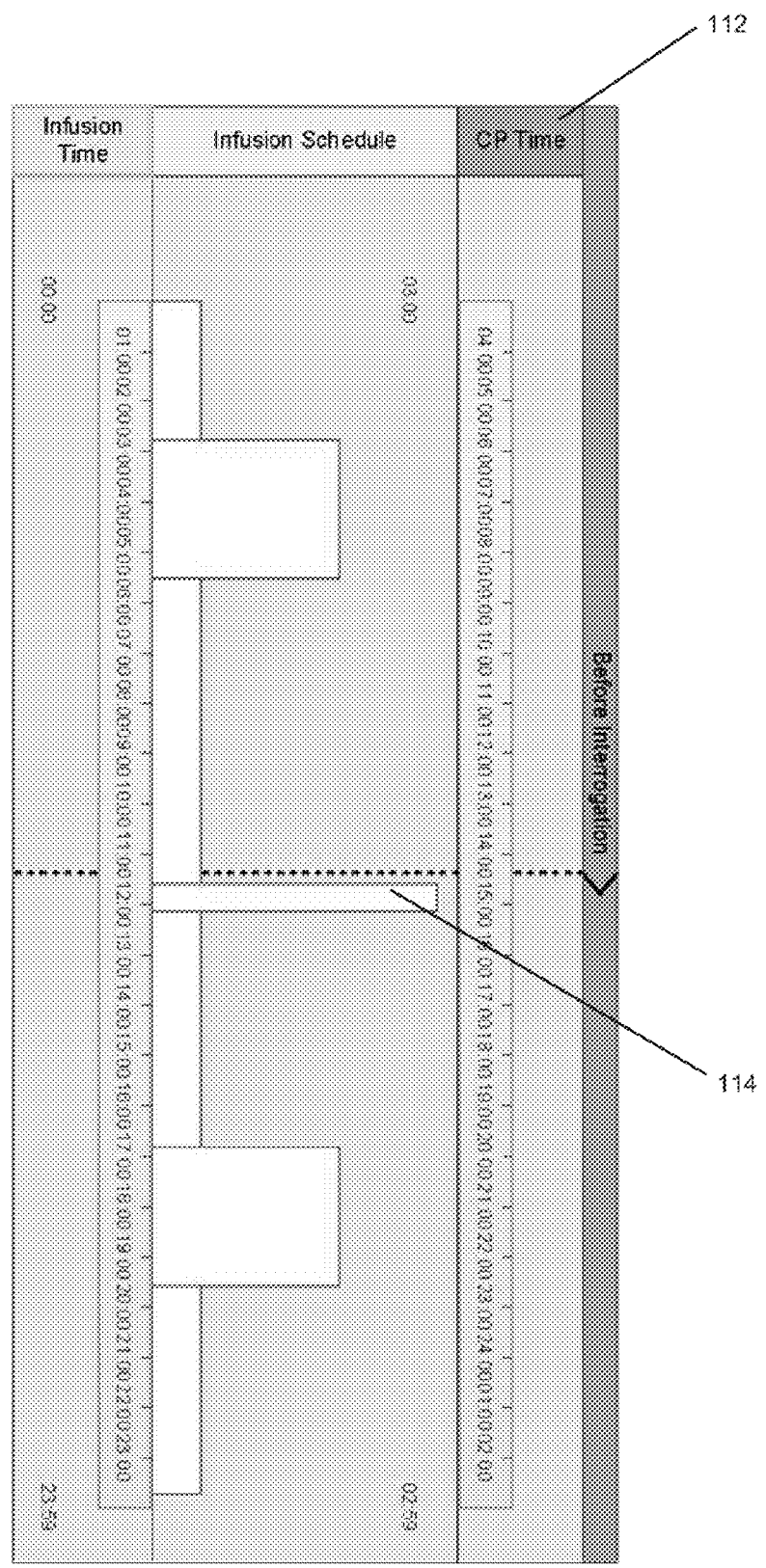
FIG. 10 is an alternative embodiment screen shot illustrating the effect of changing the clock time of the infusion device.

In certain situations, the change in clock time from the infusion device 14 to the programmer 20 may skip a timed bolus or other infusion event. As illustrated in FIG. 10, changing the infusion device 14 three hours into the future may skip a planned bolus 114 running at about 12:00 noon. In this illustration the infusion device 14 clock time is about 11:15 and the programmer 20 clock time is approximately 2:15. In this particular case the user would need to set a new bolus to run, decide to skip the bolus 114, or decide to change the infusion device 14 clock time at different time of day where the bolus would not be affected.

In the prior examples a vertical line was shown to indicate the difference between the programmer 20 clock time and the infusion device 14 clock time. As illustrated in FIG. 10, however, one line may be used to indicate the clock time for both the programmer 20 and the infusion device 14. The difference in time between the clock times is illustrated by moving the scale 112 of the programmer time further left to highlight the difference.

In one embodiment the programmer will automatically compare the programmer 20 time clock to the time clock of the infusion device 14. In further embodiments checking the clock time of the infusion device 14 may be a step that is actively selected by the user after interrogating the infusion device 14 with the programmer.

One skilled in the art can contemplate a number of ways to make sure that the clock time for the programmer 20 is accurate. Various transmitted time signals are accessible by a number of different methods, including through radio signals, the internet, global positioning system signals, atomic clock features, and others. In addition, the programmer 20 may have a manual setting in which the user can adjust the clock time.

While at least one exemplary embodiment has been presented in the foregoing detailed description of the invention, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient road map for implementing exemplary embodiments of the invention, it being understood that various changes may be made in the function and arrangement of elements described in an exemplary embodiment without departing from the scope of the invention as set forth in the appended claims and their legal equivalents.

What is claimed is:

1. A method for adjusting the clock time of an implantable device, comprising:
    establishing communication between an external device and the implantable device;
    comparing a clock time of the external device to a clock time of the implantable device and determining whether a discrepancy exists;
    determining whether the discrepancy is less than a pre-determined threshold;
    updating the clock time of the implantable device if the discrepancy is less than the pre-determined threshold;
    informing a user of the discrepancy when the discrepancy is more than the pre-determined threshold; and
    allowing the user to determine whether to update the clock time.

2. The method of claim 1 wherein informing the user of the discrepancy further comprises graphically illustrating to the user the discrepancy between the external device clock time and the implantable device clock time by showing an effect on a delivery of therapy.

3. The method of claim 2 further comprising providing the user selectable options for implementing an update to the clock time of the implantable device.

4. The method of claim 3 wherein providing the user selectable options further comprises allowing the user to decline to update the clock time of the implantable device.

5. The method of claim 3 wherein providing the user selectable options further comprises allowing the user to immediately adjust the clock time forward or backwards to match the external device clock time.

6. The method of claim 3 further comprising suggesting a new simple continuous rate of therapy delivery, and a time period for the same, to reduce the impact of adjusting the clock time of the implantable device on the delivery of therapy.

7. The method of claim 3 wherein providing the user selectable options further comprises allowing the user to select a time in the future for the clock time of the implantable device to be adjusted.

8. The method of claim 3 wherein providing the user selectable options further comprises allowing the user to set a program to incrementally adjust the time whereby the clock time of the implantable device is set to gain or lose a predetermined amount of time per selected time period until the clock time for the implantable device is adjusted to the external device clock time.

9. A method for updating the clock time of an implantable device, comprising:
    establishing connection between an external device and the implantable device;
    comparing a clock time of the external device to the clock time of the implantable device and determining whether a difference exists;
    informing a user if a difference exists;
    determining the impact on a delivery of therapy if the clock time of the implantable device is adjusted to the clock time of the external device;
    informing the user of the impact;
    requesting input from the user based upon the impact; and
    updating the clock time of the implantable device based upon the user's input.

10. The method of claim 9 further comprising providing selectable options for implementing an update to the clock time of the implantable device.

11. The method of claim 10 wherein providing selectable options further comprises allowing the user to immediately adjust the clock time forward or backwards to match the external device clock time.

12. The method of claim 10 further comprising suggesting a new simple continuous rate of therapy delivery for a period of time to reduce the impact of adjusting the clock time of the implantable device on the delivery of therapy.

13. The method of claim 10 wherein providing selectable options for how to update the clock time of the implantable device further comprises allowing the user to select a time in the future for the clock time of the implantable device to be adjusted.

14. The method of claim 10 wherein providing selectable options further comprises allowing the user to set a program to incrementally adjust the time by adjusting the time by gaining or losing a set amount of time per selected time period until the clock time for the implantable device is adjusted to the external device clock time.

* * * * *